US006647343B1

(12) United States Patent
Guthrie et al.

(10) Patent No.: US 6,647,343 B1
(45) Date of Patent: Nov. 11, 2003

(54) TEMPORAL PROFILE ANALYSIS OF MASS DATA IN A MASS SENSOR SYSTEM

(75) Inventors: Edward J. Guthrie, Lincoln University, PA (US); Charles R. Knipe, Jr., Collegeville, PA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/301,871

(22) Filed: Apr. 29, 1999

(51) Int. Cl.[7] ................................................ A61B 5/097

(52) U.S. Cl. ........................... 702/30; 702/19; 702/183; 702/179; 702/196; 702/75

(58) Field of Search ............................... 702/19, 22–24, 702/26–28, 30–35, 38, 50, 75–77, 179, 183, 196, FOR 115–119, FOR 131, FOR 134–135, FOR 139–140, FOR 168, FOR 170–171; 700/272; 422/58; 73/169

(56) References Cited

U.S. PATENT DOCUMENTS

| | | | | | |
|---|---|---|---|---|---|
| 4,075,475 | A | * | 2/1978 | Risby et al. | 250/282 |
| 4,902,891 | A | * | 2/1990 | Vestal | 250/281 |
| 5,545,895 | A | | 8/1996 | Wright et al. | |
| 5,680,321 | A | * | 10/1997 | Helmer et al. | 364/499 |
| 5,710,713 | A | | 1/1998 | Wright et al. | |
| 5,842,150 | A | * | 11/1998 | Renberg et al. | 702/23 |
| 5,850,623 | A | * | 12/1998 | Carman, Jr. et al. | 702/28 |
| 5,872,357 | A | * | 2/1999 | Flanagan | 250/252.1 |
| 5,933,792 | A | * | 8/1999 | Anderson et al. | 702/32 |
| 5,946,640 | A | * | 8/1999 | Goodacre et al. | 702/87 |
| 5,957,858 | A | * | 9/1999 | Micheels et al. | 600/529 |
| 5,965,888 | A | * | 10/1999 | Engstrom et al. | 250/339.09 |
| 6,049,762 | A | * | 4/2000 | Ganz et al. | 702/104 |
| 6,096,553 | A | * | 8/2000 | Heald et al. | 436/40 |
| 6,116,080 | A | * | 9/2000 | Logue et al. | 73/24.05 |
| 6,138,082 | A | * | 10/2000 | Wang et al. | 702/109 |

FOREIGN PATENT DOCUMENTS

| | | |
|---|---|---|
| WO | WO98/09148 | 3/1998 |
| WO | WO 9844536 | 10/1998 |

OTHER PUBLICATIONS

Wolf Muenchmeyer, Andreas Walte, Gerhard Matz, Jens Lehne "Fast Analysis of Complex Mixtures with Membrane Inlet Mass Spectrometry and Neural Networks,"WMA Airsense, Analysentechnik, GmbH.

B. Dittmann, S. Nitz, G. Horner, "A new chemical sensor on a mass spectrometric basis," Advances in Food Sciences (Adv. FoodSci (CMTL)) vol. 20, No 3/4, 69–136, May 1998, pp 115–121.

Pirouette, "Multivariate Data Analysis for Windows 95/98 and NT," Version 2.5, Copyright 1985–1998 by Informetrix, Inc.

* cited by examiner

*Primary Examiner*—Marc S. Hoff
*Assistant Examiner*—Carol S Tsai

(57) ABSTRACT

A sample may be analyzed by sampling a quantity of the sample so as to provide a respective quantity of vapor phase molecules of the respective complex sample to a, mass sensor; performing a succession of scans of the sample, so as to generate a respective series of mass spectra; compiling a k×n vector matrix representative of a plurality of temporal profiles derived from the plurality of mass spectra; performing one or more multivariate data analysis routines with respect to the vector matrix; and, in response to the multivariate data analysis routine, reporting the results of the analysis.

3 Claims, 4 Drawing Sheets

TEMPORAL PROFILE ANALYSIS OF MASS DATA IN A MASS SENSOR SYSTEM

FIELD OF THE INVENTION

The present invention relates to sample analysis systems and, more particularly, to a mass sensor system for analyzing an unknown sample according to one or more temporal profiles of mass abundance derived from mass spectra.

BACKGROUND OF THE INVENTION

Data representative of an unknown sample is generated by modern instruments for use in a wide variety of quantitative and qualitative data analyses.

Instrumentation for carrying out mass spectral analyses are known in the art for identifying one or more specific chemical components of a sample mixture according to a mass spectrum derived from the detection of a mass fragment pattern. In a typical procedure for mass spectral analysis, the sample is vaporized into a headspace volume, the concentration of vaporized components are deliberately allowed to equilibrate and stabilize, a portion of the vaporized components are withdrawn from the headspace at a predetermined time, and the vaporized portion is provided to the detection chamber in the mass spectrometer. The mass spectral analysis is then performed to generate a mass spectrum.

Often, at least one of two goals can be identified for such mass spectral data analysis: (1) comparing one or more samples to a standard having a known, or approved, composition so as to classify, if not identify, each sample; and (2) with regard to a sample that has been classified, providing an accurate identification of the component(s) in a sample that caused such sample to be classified as a differentiated, or anomalous complex sample.

To accomplish these goals, modern pattern recognition techniques have been used to interpret the data. For example, one object is to discern a pattern from the relative intensities of the sequence of peaks in the mass spectrum in a fashion sufficient to identify a "chemical fingerprint". Chemical fingerprinting, whether interpreted by human intervention or automated pattern recognition in software, has been applied to identify a sample, to infer a property of interest (typically, adherence to a performance standard), or to classify the sample into one of several categories (good versus bad, Type A versus Type B, etc.). One field of study which encompasses this type of pattern recognition technology is called chemometrics.

However, the foregoing approach is typically performed using a sample portion withdrawn at one predetermined moment after equilibration of the volatile components in the headspace. This approach presumes that a mass spectrum of a sample taken at a predetermined time after equilibration affords sufficient mass spectral information to successfully identify, classify, or otherwise analyze the unknown sample.

SUMMARY OF THE INVENTION

We have determined that a mass spectrum derived at a predetermined time after equilibration provides less than sufficient mass spectral information to successfully identify, classify, or otherwise analyze the unknown sample.

According to the present invention, a method may be carried out for performing chemometric analysis of a sample, wherein the method includes the steps of: performing a plurality (k) of ion scan sequences over a predetermined time period and generating, in response, a respective plurality of (k) mass spectra, wherein each mass spectrum is representative of the mass sensor response to the vapor phase molecules during the time period, selecting a plurality of (n) active masses from the plurality of (k) mass spectra; compiling a distinctive, k×n vector matrix that is representative of the mass sensor response to the sample; and performing a chemometric data analysis of the k×n vector matrix using one or more selectable chemometric data analysis techniques, and, in response to the chemometric data analysis, reporting the results of the chemometric data analysis.

BRIEF DESCRIPTION OF THE DRAWINGS

In the drawings and in the following detailed description of the invention, like are identified with like reference numerals. Note that the term "mass-to-charge ratio" elements may be considered herein to be interchangeable with the term "m/z ratio"; both of these terms have been shortened to "mass" for ease of description herein. Note that, for the purpose of clarity in illustration, FIGS. 2A and 2B are representative of the results of exemplary data analysis performed according to the present invention; in actual practice, the actual data, plots, and other representations of the results of an actual data analysis will vary from those illustrated.

DETAILED DESCRIPTION OF THE PREFERRED EMBODIMENTS

The method of the present invention may be employed to improve the analysis (e.g., identification or classification) of a variety of sample components present in a complex sample. Such a quantity of sample typically occurs in the form of a gas, liquid, a multiple component gases or liquid, or a mixture thereof, although the term "sample" as used herein is not limited to such forms and accordingly refers to any material susceptible to the generation of vapor phase molecules.

Figure 1:
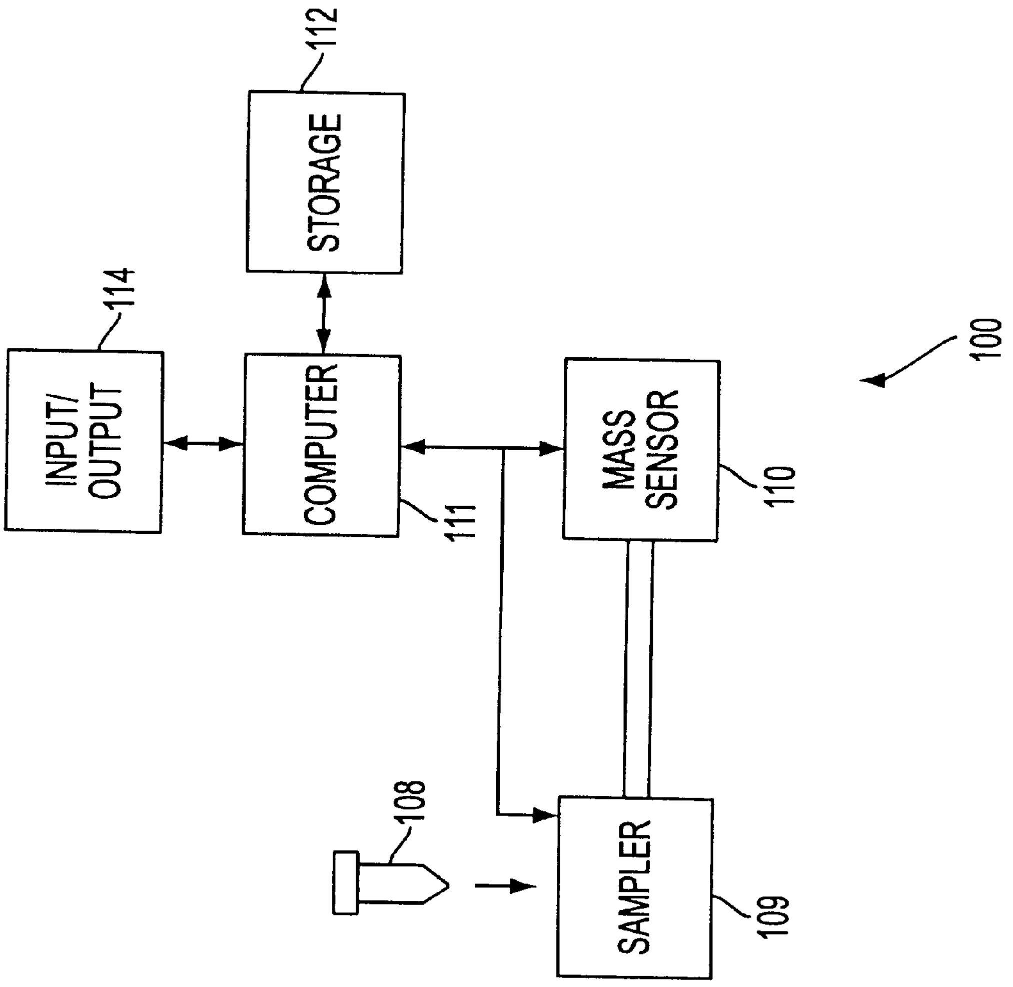
FIG. 1 is a simplified schematic representation of a mass sensor system constructed according to the present invention.

A preferred embodiment of a mass sensor system 100 constructed according to the present invention is illustrated in FIG. 1. The system 100 is useful for analysis of a sample provided in a respective sample container 108. The system 100 includes a sample introduction means 109, a mass sensor apparatus 110, a computer 111, an information input/output means 114, and an information storage means 112. Preferably, the output signal of the mass sensor 110 is provided in the form of a first data matrix to be analyzed by the computer 111 with use of a novel sample component identification method described herein that is based on multivariate data analysis, with the ultimate analytical results, i.e., the subsequent classification or identification of the sample component of interest, being reported to the operator by way of the input/output means 114, the storage means 112, or by suitable devices known in the art.

The computer 111 may include one or more computing devices amenable to the practice of this invention, e.g., one or more computing devices such as microprocessors, micro-controllers, switches, logic gates, or any equivalent logic device capable of performing the computations described hereinbelow. The input/output means 114 preferably includes a keyboard, keypad, or computer mouse, or network connection to a remote processor (not shown) for transfer of operating condition parameters, analytical data and results, system data, and the like. Information input/output means 114 may include display means such as an alphanumeric or video display, a printer, or similar means. The preferred computer 111 may have the storage means 112 integrated therein, such that the storage means 112 is provided in the form of volatile and non-volatile memory devices in which input and output information, operating condition parameters, system information, and programs can be stored and retrieved. Operating commands, device and sample type information, mass sensor response attributes, data libraries, selectable data transformations, multivariate data analysis programs, and other information necessary to perform the analysis described herein may be transferred to and from the computing means 111 by way of the input/output means 114 or the storage means 112. Messages prompting the operator to enter certain information, such as a desired operating parameter or analytical step can be generated by the processor 111 and displayed on the input/output device 114. The system 100 may further comprise other devices (not shown) such as a stand-alone power system, network and bus system (input/output or I/O) controllers, isolation devices, data and control interface cards, remote telemetry electronics, and other related electronic components for performing control, data processing, and communication tasks beyond those described herein, as known in the art.

A preferred embodiment of the system 100 employs an integrated sampler and mass selective detector provided in the form of the HP 4440A Chemical Sensor from Hewlett-Packard Co., Wilmington, Del. The HP 4440A Chemical Sensor includes a sampler 109 provided in the form of a modified headspace sampler (e.g., a Hewlett-Packard 7694 Automated Headspace Autosampler) that is coupled directly to a mass sensor 110 provided in the form of modified mass selective detector (e.g., a Hewlett-Packard 5973 Mass Selective Detector). Computer 111 preferably is provided in the form of a personal computer such as a Hewlett-Packard Vectra XA Series desktop computer coupled to the mass sensor 110. Unlike traditional headspace gas chromatographic instruments with mass selective detection (known as a HS/GC/MS system), the system 100 operates without a gas chromatograph and accordingly need not effect a separation of the volatile constituents. Headspace volatiles are transferred directly to the mass sensor 110, which typically gives rise to a mass sensor response that is representative of all the volatile constituents that are subject to ionization.

An ion scan sequence implemented by the system 100 (also described herein as a scan) may be understood as follows. Volatiles are swept out of the sampler 109 into the mass sensor 110 wherein the vapor phase molecules are ionized and fragmented, and the charged fragments are drawn to an integral ion detector. Monitoring the ion detector's output current (which represents ion abundance) as a function of the ion mass to charge ratio (symbolized as m/z and described herein as "mass") gives rise to a mass spectrum. Each mass spectrum is representative of the mass sensor response to the vapor phase molecules present in the detector chamber during the time of the respective scan. A plurality of, i.e., a series of scans, generates a respective series of mass spectra that is representative of the mass sensor response to the vapor phase molecules developed in the mass sensor 110 during the time period within which the series of scans is performed.

Preferred embodiments of the sample container 108 include a 10 or 20 ml vial. The HP 4440A chemical sensor can accommodate a group of up to 44 of such sample containers for unattended operation. Because there is no separation or quantitation involved in the analysis, and because the mass sensor 110 is capable of fast scanning, it is possible to obtain plural scans of a single sample and to complete such an analysis of each sample within about three minutes. Virtually any sample that fits into an appropriate sample container 108 and produces a volatile when heated is suitable for the illustrated sampling technique. Of course, the present invention contemplates the use of other embodiments of the sampler 109 known to those skilled in the art, including, but not limited to, devices such as: liquid sample introduction using a membrane; gaseous sample injection; or thermal desorption.

Figure 2A:
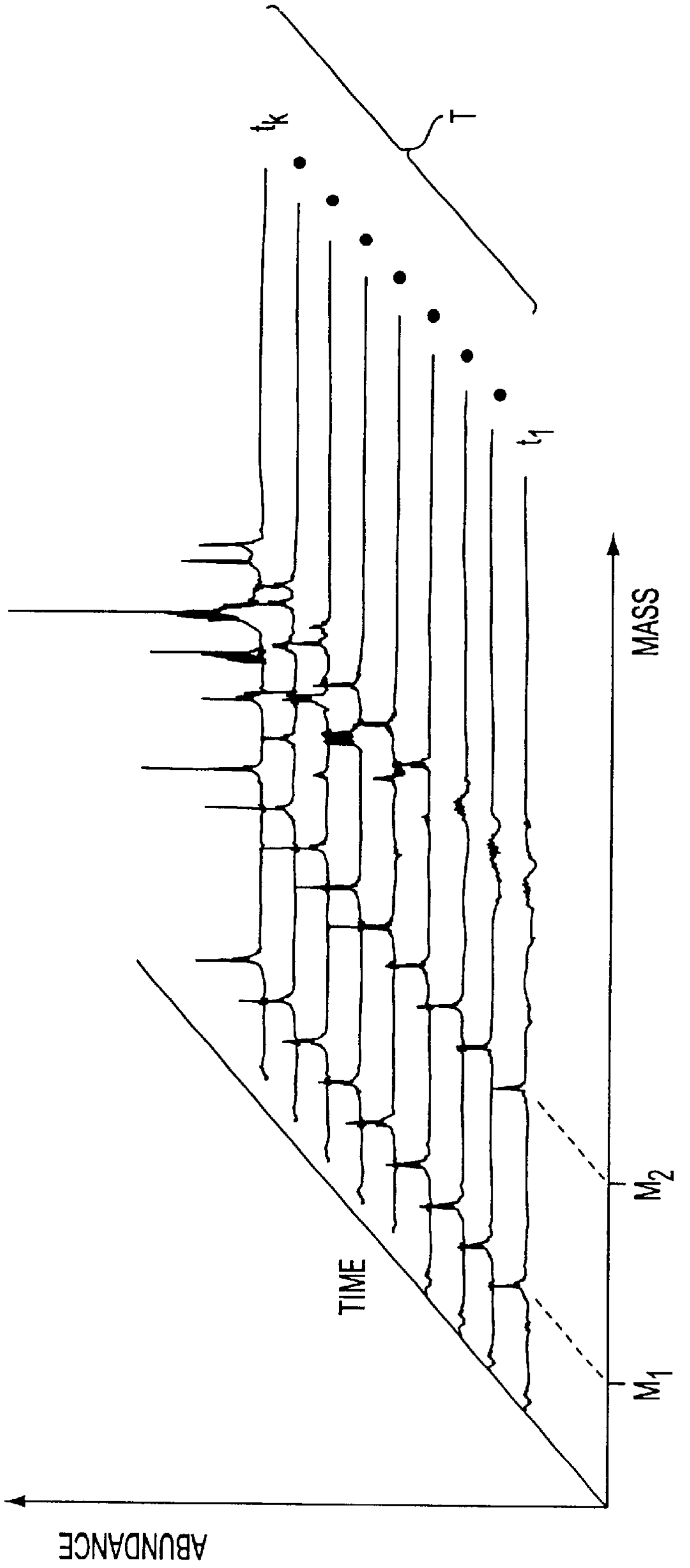
FIG. 2A is a graphical representation of the results obtained in a series of mass spectral analyses of a vaporized sample, performed in the system of FIG. 1 over a period of time, wherein each scan represents a plot of ion abundance versus mass.
Figure 2B:
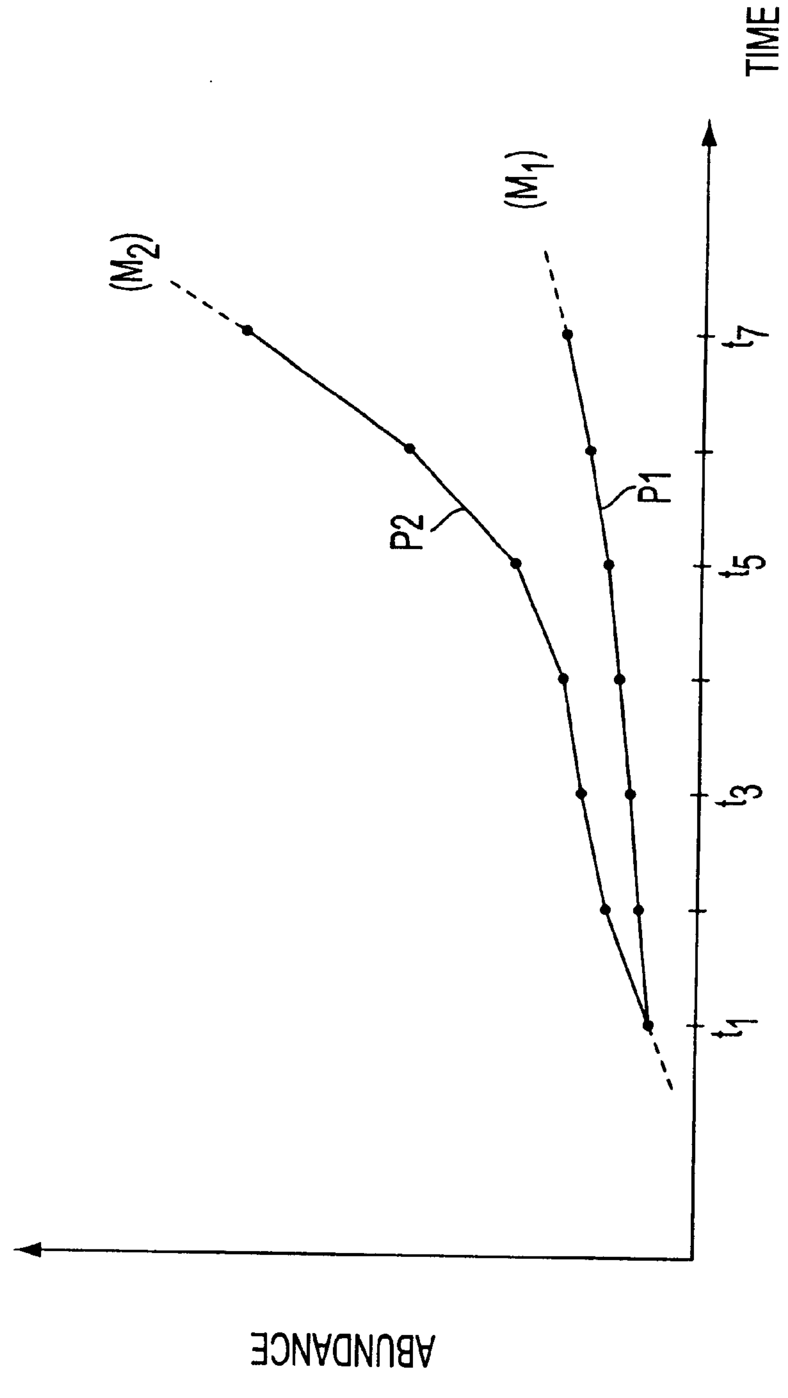
FIG. 2B is a graphical representation of the temporal profiles of ion abundance of two masses ($m_1$ and $m_2$) selected from a k×n vector matrix of temporal profiles that is characteristic of, if not uniquely associated with, the spectral response of the mass sensor to the sample.
Figure 3:
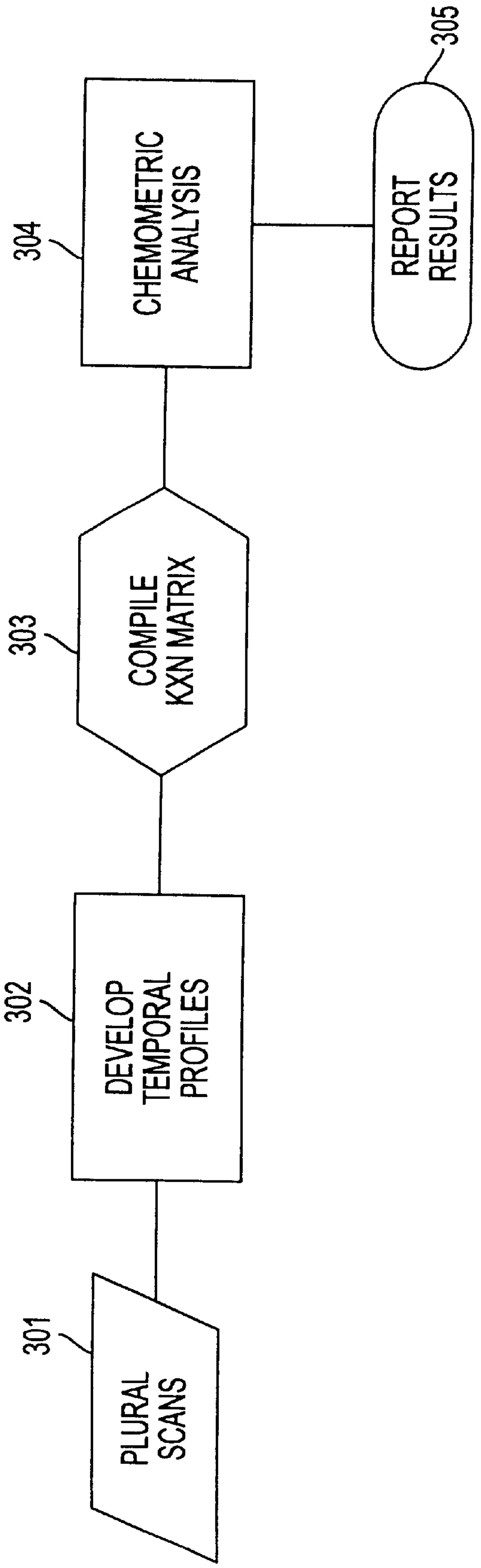
FIG. 3 is a block diagram of a method for developing a vector matrix and for performing multivariate data analysis of the vector matrix in the mass sensor system of FIG. 1.

Turning now to FIGS. 2–3, according to a primary aspect of the present invention, and in a significant departure from the prior art, the sample may be understood to be susceptible to a novel analytical method.

As illustrated in FIG. 2A, and as described in step 301 in FIG. 3, the vapor phase molecules from the sample are preferably subjected to a series of k scans (performed at times $t_1$ through $t_k$) such that a series of k respective mass spectra is then derived. The resulting mass spectra are thus representative of the composition of the vapor phase molecules that developed from the sample over a period of time $T=(t_k-t_1)$.

Mass information may be extracted from the resulting mass spectra to construct temporal profiles useful for detecting a change in abundance of certain masses (for example, masses $m_1$ and $m_2$) due to, e.g., a corresponding volatilization of the vapor phase molecules over time. For example, in certain applications, the series of ion detector scans may be initiated at the onset of volatilization without resort to the equilibration or stabilization periods found in the prior art. As a $result_1$ distinctive temporal profiles representative of the changing abundance of certain masses during early stages of volatilization in a fashion that would otherwise not be detected.

As illustrated in FIG. 2B, a plurality of n abundance values, each of which correspond to the abundance of a selected mass detected at a respective time $t_1, t_2 \ldots, t_k$, may be plotted to discern respective temporal profiles (such as first and second profiles P1 and P2 shown in FIG. 2B), are compiled to distinguish the changes in the abundance of certain masses over a selected time period. (Note, for example, the differing rates of increase of abundance for masses $m_1$ and $m_2$ during the time period from $t_1$ to $t_7$. These differing rates of increase of abundance would not be detected in a conventional mass spectral analysis technique that forces equilibration of volatilization during the time period from $t_1$ to $t_7$.) These profiles may be subjected to the chemometric and related data analysis techniques described herein to identify or classify the sample.

Furthermore, and as denoted in step 302, by selecting a plurality of (n) active masses from the plurality of (k) mass spectra, each mass spectrum may be represented as a n dimensional vector of the following form:

$$X(j)=x_1, x_2, \ldots, x_n$$

wherein the individual components ($x_1$, $x_2 \ldots$, $x_n$) of the pattern vector are observable quantities, for example, $x_1$ is set equal to the intensity of the peak (i.e., abundance) that is detected at a first mass, $x_2$ is set equal to the intensity of the peak (i.e., abundance) that is detected at a second mass, and so on.

As denoted in step 303, the mass spectral response obtained from a succession of k scans allow the compilation of a distinctive, k×n vector matrix that is uniquely representative of the mass sensor spectral response to the vapor phase molecules during the time period T. Hence, the k×n vector matrix can convey the aggregate body of information represented by the above-described temporal profiles and accordingly is based in the time domain.

FIG. 2B illustrates a portion of such a k×n vector matrix, wherein the abundance vectors for two exemplary masses, $m_1$ and $m_2$ are plotted so as to form two respective temporal profiles (P1 and P2), each of which convey heretofore undetected information about the sample. For example, at time $t_1$, the abundance vectors of masses ml and $m_2$ are substantially equivalent. However, repeated scans during the time period from $t_1$ to $t_7$ indicate that the abundance vectors of masses $m_1$ and $m_2$ diverge considerably with the passage of time, such that the abundance vector for mass $m_2$ at time $t_k$ substantially exceeds that of mass $m_1$ time $t_k$. Whereas FIG. 2B illustrates only a portion of such a k×n vector matrix, one may appreciate that the complete k×n vector matrix forms an aggregate record of a plurality of temporal profiles, Accordingly, the k×n vector matrix is considered to be characteristic of, if not uniquely associated with, the spectral response of the mass sensor to the sample. As the dimensionality of the k×n vector matrix is increased (by, for example, selecting a sufficient number of masses and scans), the k×n vector matrix becomes uniquely representative of the sample and therefore is susceptible to an application (in step 304) of one or more multivariate data analysis techniques so as to yield classification or identification of the sample.

One exemplary embodiment of a multivariate data analysis routine will now be discussed, although it is to be understood that the following description is exemplary and not meant to be limiting, as other routines are known and customarily performed by those skilled in the art of chemometric analysis.

The k×n vector matrix may first be subject to preprocessing by use of a time-domain-to-frequency-domain transformation to provide a secondary data matrix that is, like the k×n vector matrix, representative of the spectral response of the mass sensor to the sample, but based in the frequency domain. Preferred embodiments of the selected transform include the discrete or real value Fourier transform and the Fast Fourier Transform (FFT). (Other useful transforms known to those skilled in the art include the Walsh function, Hadamard transform, and the like.)

The secondary data matrix may then be subjected to one or more multivariate data analysis techniques known in the art of chemometrics to discern one or more informative characteristics of the second data matrix to enable identification or classification of the sample.

As denoted in step 305, the results of the multivariate data analysis, i.e., indicia representative of the identity or class associated with the sample, may then be reported on the input/output means 114 or stored in the storage means 112 for later retrieval.

A preferred embodiment of a comprehensive chemometrics modeling software package is commercially available in the form of "Pirouette for Windows" from Infometrix, Inc., of Woodinville, Wash. Prediction, classification, data exploration and pattern recognition methods are operable in this software package. The preferred software package also includes an interface that facilitates interacting with raw and processed data. Another useful chemometrics modeling software packages is commercially available from UMETRI, of Umeå, Sweden, which produces a graphically-oriented software known as "SIMCA-P" that is useful for effecting Design Of Experiments (DOE), Multivariate Data Analysis (MVDA), and modeling.

Chemometrics is considered herein the field of extracting information from multivariate chemical data using tools of statistics and mathematics. Chemometric tools are typically used for one or more of three primary purposes: to explore patterns of association in data; to track properties of materials on a continuous basis; and to prepare and use multivariate classification models. The algorithms in primary use in the art of chemometrics have demonstrated a significant capacity for analyzing and modeling a wide assortment of data types for an even more diverse set of applications. Patterns of association exist in many data sets, but the relationships between samples can be difficult to discover when the data matrix exceeds three or more features. Exploratory data analysis can reveal hidden patterns in complex data by reducing the information to a more comprehensible form. Exploratory data analysis is the computation and the graphical display of patterns of association in multivariate data sets. The algorithms for this exploratory work are designed to reduce large and complex data sets into a set of best views of the data; these views provide insight into the structure and correlation that exist among the samples and variables in the data set. Accordingly, one skilled in the art may choose to include an implementation of a chemometric analysis so as to expose possible outliers and indicate whether there are patterns or trends in the data.

Many applications require that samples be assigned to predefined categories, or "classes". This may involve determining whether a sample is good or bad, or predicting an unknown sample as belonging to one of several distinct groups. Accordingly, such classification may be performed in the control and chemometrics software operable in system 100 for the computation and the graphical display of class assignments based on the multivariate similarity of one sample to others. The algorithms for this classification work are designed to compare new samples against a previously analyzed experience set. A classification model is used to predict a sample's class by comparing the sample to a previously analyzed experience set, in which categories are already known. K-nearest neighbor (KNN) and soft independent modeling of class analogy (SIMCA) are primary chemometric techniques selectable for this purpose. In this manner, a chemometric system can be built that is objective and thereby standardize the data evaluation process. Exploratory algorithms, such as principal component analysis (PCA), which is also known as factor analysis, are also contemplated for reducing one or more k×n data matrices into a series of optimized and interpretable views, and a principal components analysis algorithm is preferably included as one of the multivariate analysis routines in the control and chemometrics software in the computer 111.

In principal component analysis, the composite spectrum of a sample becomes a data point on a three-dimensional PCA plot. The data point from similar samples can be expected to cluster together on the plot. Principal components are considered "factors" in the plots. Samples that differ in their volatile components (due to composition, grade, impurity, manufacturing processes, etc.) will cluster in different locations on the three-dimensional PCA plot. One can then view sample clusters and outliers by simply rotating the three-dimensional plot on the computer display. Principal component analysis is designed to provide the best possible view of the variability in a multivariate data set. In addition, the intrinsic dimensionality of the data can be determined and, with variance retained in each factor and the contribution of the original measured variables to each, this information can be used to assign chemical meaning (or biological meaning or physical meaning) to the data patterns that emerge and to estimate what portion of the measurement space is noise.

Further information concerning classification analysis may be found in Forina, M. and Lanteri, S., "Data Analysis in Food Chemistry" in B. R. Kowalski, Ed., *Chemometrics, Mathematics and Statistics in Chemistry* (D. Reidel Publishing Company, 1984), 305349. Sharaf, M. A.; lllman, D. L.; and Kowalski, B. R.; *Chemometrics* (Wiley: New York, 1986).

Further information concerning multivariate data analysis in general may be found in Chatfield, C., and Collins, A. J., *Introduction to multivariate analysis* (1980); Höskuldsson, Agnar, *Prediction Methods in Science and Technology*, Thor Publishing Denmark (1996); Jackson, J. E., *A user's guide to principal components*, John Wiley (1991); Jollife, I. T. *Principal component analysis*, Springer-Verlag (1986); Martens, H., and Naes, T., *Multivariate calibration*, John Wiley (1989).

The instrument control software and chemometrics software are used not only for carrying out the multivariate data analysis but also for control of the system 100 and for the collection and management of the data. For example, as a set of scans is compiled, each mass spectrum may be automatically appended to a single file in preparation for compilation as the k×n vector matrix prior to the transformation and multivariate data analysis routines. Also, by use of software-based control routines which are tailored to coordinate the functions of the sampler 109 and the mass sensor 110, the operator can create one or more distinctive analytical methods each of which specify the controlling instrument parameters and the configuration an analytical sequence for one or more samples.

In addition, the full functionality of the chemometrics software package is present in the background to provide access to additional tuning and signal processing features. For example, although the system 100 is designed to operate over a wide, user-selectable mass range of 2 to 800 amu, a more limited mass range may be selected (such as a range of about 35 to 180 amu may be used to limit the effects of water or air on the integrity of the data.)

It will be accordingly be understood that the system 100 is operable with use of one or more of the multivariate data analysis techniques described herein, for classification of a plurality of complex samples and for identification of, for example, an anomalous sample component in a selected complex samples.

Although certain embodiments of the present invention have been set forth with particularity, the present invention is not limited to the embodiments disclosed. Accordingly, reference should be made to the appended claims in order to ascertain the scope of the present invention.

What is claimed is:

1. The method comprising the steps of:

providing a sample not in equilibria to a mass sensor as the sample is changing state;

performing a succession of scans to generate mass spectra of volatile vapor phase constituents generated as the sample is changing state over time;

obtaining a temporal profile of charged constituents formed as a result of the succession of the scans that generated the mass spectra, the temporal profile being at least partially representative of the mass sensor response to the sample;

performing a multivariate data analysis routine with respect to the temporal profile; and supplying results of the multivariate data analysis routine.

2. The method of claim 1, further comprising the step of subjecting the temporal profile to preprocessing by use of a time-domain-to-frequency domain transformation to provide a secondary data matrix that is representative of the spectral response of the mass sensor to the sample in the frequency domain.

3. The method of claim 2, wherein the time-domain-to-domain transform is selected from the group consisting of: the discrete Fourier transform, the real value Fourier transform, and the East Fourier Transform (FFT).

* * * * *